(12) United States Patent
Beaurain et al.

(10) Patent No.: US 9,763,699 B2
(45) Date of Patent: *Sep. 19, 2017

(54) SPINAL OSTEOSYNTHESIS DEVICE AND PREPARATION METHOD

(71) Applicant: LDR MEDICAL, Rosières Près Troyes (FR)

(72) Inventors: Jacques Beaurain, Saulon la Chapelle (FR); Joel Delecrin, Vertou (FR); Michel Onimus, Besancon (FR); Isabelle Koenig, L'Etrat (FR); Alain Ducolombier, Antony (FR); Marc Pierunek, Montpellier (FR); Herve Chataigner, Boussieres (FR); Marielle Derosi, Perols (FR); Agnes DePostel, Waly (FR)

(73) Assignee: LDR Medical, Sainte-Savine (FR)

( * ) Notice: Subject to any disclaimer, the term of this patent is extended or adjusted under 35 U.S.C. 154(b) by 359 days.

This patent is subject to a terminal disclaimer.

(21) Appl. No.: 13/873,190

(22) Filed: Apr. 29, 2013

(65) Prior Publication Data

US 2014/0148855 A1 May 29, 2014

Related U.S. Application Data

(63) Continuation of application No. 12/409,327, filed on Mar. 23, 2009, now Pat. No. 8,430,915, which is a (Continued)

(30) Foreign Application Priority Data

Apr. 6, 2001 (FR) ..................... 01 04717

(51) Int. Cl.
    *A61B 17/70* (2006.01)

(52) U.S. Cl.
    CPC ........ *A61B 17/7037* (2013.01); *A61B 17/701* (2013.01); *A61B 17/7034* (2013.01); (Continued)

(58) Field of Classification Search
    CPC ............ A61B 17/7037; A61B 17/7034; A61B 17/701; A61B 17/7041; A61B 17/7004; A61B 17/7002
    See application file for complete search history.

(56) References Cited

U.S. PATENT DOCUMENTS

| 1,022,999 A | 4/1912 | Bashaw |
| 1,191,676 A | 7/1916 | Maggio |

(Continued)

FOREIGN PATENT DOCUMENTS

FR    2802796    6/2001

OTHER PUBLICATIONS

Apparatus and Method for Fusing Opposing Spinal Vertebrae, Bramlet, Dale G. et al., U.S. Appl. No. 09/635,436, filed Aug. 11, 2000.

(Continued)

*Primary Examiner* — Christopher Beccia
(74) *Attorney, Agent, or Firm* — Lauff Law PLLC

(57) ABSTRACT

A spinal internal implantation device for osteosynthesis has one or more bars for supporting for moving the spine and at least one implant for connecting the bars and vertebrae. The implant includes a blown anchor attached to a body of the implant and a fixation arrangement for the bars. The fixation arrangement includes a clamp for clamping the bar against internal walls of a channel formed in the body of the implant. At least part of the length of the bars includes a transversal bearing structure that is a cross-section of the bars having at least one flat part of a part having a lower forepost convexity than the rest of the cross section.

16 Claims, 4 Drawing Sheets

Related U.S. Application Data continuation of application No. 10/473,999, filed as application No. PCT/IB02/02827 on Apr. 3, 2002, now Pat. No. 7,507,248.

(52) U.S. Cl.
CPC ...... *A61B 17/7041* (2013.01); *A61B 17/7002* (2013.01); *A61B 17/7004* (2013.01)

(56) References Cited

U.S. PATENT DOCUMENTS

| | | | |
|---|---|---|---|
| 1,750,687 A | | 3/1930 | Pitkin |
| 4,641,636 A | | 2/1987 | Cotrel |
| 4,773,402 A | | 9/1988 | Asher et al. |
| 4,815,453 A | | 3/1989 | Cotrel |
| 5,007,880 A | | 4/1991 | Walker |
| 5,234,431 A | | 8/1993 | Keller |
| 5,282,863 A | * | 2/1994 | Burton ............... A61B 17/7007 606/254 |
| 5,360,431 A | | 11/1994 | Puno et al. |
| 5,385,583 A | | 1/1995 | Cotrel |
| 5,474,555 A | | 12/1995 | Puno et al. |
| 5,578,033 A | * | 11/1996 | Errico et al. .................. 606/276 |
| 5,591,235 A | * | 1/1997 | Kuslich ................. A61B 17/70 606/261 |
| 5,603,714 A | * | 2/1997 | Kaneda et al. ............... 606/272 |
| 5,651,789 A | * | 7/1997 | Cotrel ........................... 606/252 |
| 5,738,586 A | | 4/1998 | Arriaga |
| 5,782,833 A | | 7/1998 | Haider |
| 5,833,418 A | | 11/1998 | Shoji |
| 5,876,403 A | * | 3/1999 | Shitoto ......................... 606/308 |
| 5,910,142 A | * | 6/1999 | Tatar ............................ 606/272 |
| 5,984,928 A | | 11/1999 | Hermann |
| 6,045,921 A | | 4/2000 | Restaino et al. |
| 6,074,393 A | * | 6/2000 | Sitoto .......................... 606/307 |
| 6,187,005 B1 | | 2/2001 | Brace et al. |
| 6,264,658 B1 | | 7/2001 | Lee et al. |
| 6,458,132 B2 | * | 10/2002 | Choi ................. A61B 17/7032 606/267 |
| 6,475,218 B2 | * | 11/2002 | Gournay et al. .............. 606/272 |
| 6,520,963 B1 | | 2/2003 | McKinley |
| 6,547,789 B1 | * | 4/2003 | Ventre et al. ................. 606/308 |
| 6,554,834 B1 | | 4/2003 | Crozet et al. |
| 8,221,457 B2 | | 7/2012 | Delecrin et al. |
| 8,920,474 B2 | | 12/2014 | Delecrin et al. |
| 2002/0143341 A1 | | 10/2002 | Biedermann et al. |
| 2004/0254577 A1 | * | 12/2004 | Delecrin ............ A61B 17/7007 606/261 |
| 2005/0171537 A1 | | 8/2005 | Mazel et al. |
| 2006/0025769 A1 | | 2/2006 | Dick et al. |
| 2013/0238036 A1 | | 9/2013 | Sinha |

OTHER PUBLICATIONS

Intervertebral nucleus prothesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preparation Method, Beaurain, Jacques et al., U.S. Appl. No. 10/473,999, filed Apr. 12, 2004.
Intevertebral Disc Prosthesis and Fitting Tools, Beaurain, Jacques et al., U.S. Appl. No. 10/476,565, filed Jun. 8, 2004.
Vertebral Cage Device With Modula Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device, Delecrin, Joel et al., U.S. Appl. No.10/492,827, filed Jul. 15, 2004.
Osseous anchoring device for a prothesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disc Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S. Appl. No. 11/098,266, filed Apr. 4, 2005.
Intervertebral Disc Prosthesis, Zeegers, Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prothesis, Rashbaum, Ralph et al., U.S. Appl. No. 11/341,007, filed Jan. 27, 2006.
Intervertebral Disc Prosthesis and Instrumentation for Insertion of the Prosthesis Between the Vertebrae, Rashbaum, Ralph et al., U.S. Appl. No. 11/362,253, filed Feb. 24, 2006.
Transforaminal intersomatic cage for an intervertebral fusion graft and an instrument for implanting the cage, Davis, Reginald James et al., U.S. Appl. No. 11/378,165, filed Mar. 17, 2006.
Intervertebral nucleus prosthesis and surgical procedure for impanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with unified grafts, Huppert, Jean, U.S. Appl. No. 11/767,386, filed Jun. 22, 2007.
Nucleus Prostheses, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osetosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Intervertebral disc prosthesis insertion assemblies, Jodaitis, Alexandre et al., U.S. Appl. No. 12/527,373, filed Mar. 19, 2010.
Intervertebral implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.

(56) References Cited

OTHER PUBLICATIONS

Intervertebral Disc Prosthesis, Zeegers, M. Willem, U.S. Appl. No. 13/215,123, filed Aug. 22, 2011.
Interspinous Implant and Implantation Instrument, Dinville, Hervé et al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant and Implantation Instrument, Dinville, Hervé et al., U.S. Appl. No. 13/520,041, filed Nov. 26, 2012.
Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, Willem, U.S. Appl. No. 13/603,043, filed Sep. 4, 2012.
Intervertebral Disc Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforaminal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Intervertebral Disc Prosthesis Insertion Assemblies, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Instrument for Implanting an Interspinous Implant, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prosthesis, Vila, Thierry et al., U.S. Appl. No. 14/159,161, filed Jan. 20, 2014.
Interveterbral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.
Interspinous Implant and Instrument for Implanting an Interspinous Implant, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Cage Having Spike, Kim, Seo-Kon et al., U.S. Appl. No. 14/460,536, filed Aug. 15, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
Plate for osteosynthesis device and preassembly method, Delecrin, Joel et al., U.S. Appl. No. 14/584,674, filed Dec. 29, 2014.
Intervertebral Implant Having Extendable Bone Fixation Members, Brett, Darrell C., U.S. Appl. No. 14/594,770, filed Jan. 12, 2015.
Vertebral implant, device of vertebral attachment of the implant and instrumentation for implantation thereof, Ameil, Marc et al., U.S. Appl. No. 14/638,746, filed Mar. 4, 2015.
Intervertebral Disc Prosthesis, Zeegers, Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, Willem, U.S. Appl. No. 14/726,557, filed May 31, 2015.
Anchoring Device and System for an Intervertebral Implant, Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.
Vertebral implant, vertebral fastening device of the implant and implant instrumentation, Dinville, Herve et al., U.S. Appl. No. 14/891,322, filed Nov. 13, 2015.
Instruments and Methods for Removing Fixation Devices from Intervertebral Implants, Dinville, Herve et al., U.S. Appl. No. 14/931,007, filed Nov. 3, 2015.
Instrumentation and Methods for Inserting an Intervertebral Disc Prosthesis, Dinville, Herve, U.S. Appl. No. 15/012,815, filed Feb. 1, 2016.
Intervertebral Disc Prosthesis, Beaurain, Jacques et al., U.S. Appl. No. 15/049,934, filed Feb. 22, 2016.
Intervertebral Disc Prosthesis and Instrumentation for Insertion of the Prosthesis Between the Vertebrae, Steib, Jean-Paul, U.S. Appl. No. 15/049,995, filed Feb. 22, 2016.
Anchoring device for a spinal implant, spinal implant and implantation instrumentation, Chataigner, Hervé et al., U.S. Appl. No. 15/115,659, filed Jul. 29, 2016.
Interspinous Implant and Implantation Instrument, Dinville, Hervé et al., U.S. Appl. No. 15/145,413, filed May 3, 2016.
Implant for Osseous Anchoring with Polyaxial Head, Beaurain, Jacques et al., U.S. Appl. No. 15/145,431, filed May 3, 2016.
Intervertebral disc prosthesis, surgical methods, and fitting tools, Beaurain, Jacques et al., U.S. Appl. No. 15/150,316, filed May 9, 2016.
Interspinous Implant and Instrument for Implanting an Interspinous Implant, Dinville, Hervé et al., U.S. Appl. No. 15/225,612, filed Aug. 1, 2016.
Intervertebral Disc Prosthesis, Zeegers, M. Willem, U.S. Appl. No. 15/269,923, filed Sep. 19, 2016.
Intervertebral Implant Having Extendable Bone Fixation Members, Brett, Darrell C., U.S. Appl. No. 15/289,861, filed Oct. 10, 2016.
Vertebral implant, device for vertebral attachment of the implant and instrumentation for implantation thereof, Ameil, Marc et al., U.S. Appl. No. 15/309,197, filed Nov. 6, 2016.
Intervertebral Disc Prosthesis Insertion Assemblies, Jodaitis, Alexandre et al., U.S. Appl. No. 15/340,565, filed Nov. 1, 2016.
Nucleus Prosthesis, Vila, Thierry et al., U.S. Appl. No. 15/391,305, filed Dec. 27, 2016.

(56) References Cited

OTHER PUBLICATIONS

Plate for osteosynthesis device and preassembly method, U.S. Appl. No. 15/414,523, filed Jan. 24, 2017.
Implant for Osseous Anchoring with Polyaxial Head, Beaurain, Jacques et al., U.S. Appl. No. 15/426,938, filed Feb. 7, 2017.
Intervertebral disc Prosthesis, Zeegers, Willem, U.S. Appl. No. 15/432,795, filed Feb. 14, 2017.
System of spinal arthodesis implants, Mercier, Alexis et al., U.S. Appl. No. 15/442,591, filed Feb. 24, 2017.
Bone Implants, Lavigne, Christophe et al., U.S. Appl. No. 15/501,166.
Intervertebral Fusion Cage with Retractable-Extrudable Pins, Brett, Darrell C., U.S. Appl. No. 61/243,297, filed Sep. 17, 2009.
Intervertebral Fusion Cage with Retractable-Extrudable Pins, Brett, Darrell C., U.S. Appl. No. 61/260,364, filed Nov. 11, 2009.

\* cited by examiner

SPINAL OSTEOSYNTHESIS DEVICE AND PREPARATION METHOD

CROSS-REFERENCE TO RELATED APPLICATIONS

This application is a continuation of U.S. patent application Ser. No. 12/409,327 filed Mar. 23, 2009, and issuing as U.S. Pat. No. 8,430,915 on Apr. 30, 2013, which is a continuation of U.S. patent application Ser. No. 10/473,999 filed Oct. 6, 2003, and issuing as U.S. Pat. No. 7,507,248 on Mar. 24, 2009, which is a National Stage Entry of International Application PCT/IB02/02827, filed Apr. 3, 2002, which claims priority to French Patent Application No. 0104717, filed Apr. 6, 2001.

BACKGROUND

The present invention relates to an osteosynthesis device, particularly for spinal support or correction, that can be used in particular for internal implantation.

For spinal support or correction, a device comprising one or more support bars positioned along the spinal column is used, and fixed to certain vertebrae by implants. Said implants are fixed at one end to the bars and at the other end to the vertebrae by bone anchorage means, composed of a hook supported by a vertebra or of a threaded part screwed inside the vertebra itself, for example at the pedicle.

In such devices, it is known to use bars inserted into the body of the implant via an opening, either simply through the implant or in the form of a channel opening onto a side, said channel possibly opening onto the side or rear (on the top of the implant).

In the case of a closed type implant, the insertion of the bar must most frequently be carried out after the fixation of the implants, which requires the delicate operation of deforming the bar as it is inserted into the different implants.

In the case of an implant with a side or rear opening, the bar-implant fixation may be obtained by means of an intermediate part referred to as a clamp. Said clamp is formed from a ring which is inserted around the bar and fixed to it by a clamping screw, said clamp in turn being inserted into the opening of the implant longitudinally along the axis of the bar. Once the clamp is inserted longitudinally in the implant, as in patent FR 2 545 350, the clamping is obtained by a conical shank and secured by an additional part referred to as a safety lock. Failing a safety lock, as in patent EP 0 392 927, the clamping is secured by two additional screws clamped onto the bar via the clamp and the body of the implant.

Another possibility consists of inserting the bar directly into an implant with a rear open channel, as in patent FR 2 680 461, and clamping this bar with a threaded plug securing the bar by means of a curved blade to provide a satisfactory contact surface.

In both cases, this assembly of several parts is intended to ensure the reliability of the clamping, but represents a complexity and size liable to render implantation delicate, particularly at the junction of the lumbar and sacral regions where only a small amount of space is available due to anatomical conditions. The presence of small parts to assemble during the operation involves the disadvantage of more delicate manipulations and the risk of said small parts being disseminated in the operative field.

SUMMARY

An aim of the present invention is to remedy the drawbacks of the prior art by providing an osteosynthesis device enabling easier adjustment on the operative site and more rapid implantation.

Another aim is to provide a more compact osteosynthesis device.

Another aim is to provide an osteosynthesis device comprising a reduced number of separate parts during implantation.

Another aim is to provide an osteosynthesis device wherein the clamping or fastening shows improved reliability.

BRIEF DESCRIPTION OF THE DRAWINGS

The invention, with its characteristics and advantages, will be seen more clearly upon reading the description with reference to the appended figures wherein.

DETAILED DESCRIPTION OF THE DRAWINGS

The osteosynthesis device according to the invention uses the principles of the prior art in terms of the possible application. It can be adapted to screw or hook implants and will be represented here in the case of screw, or pedicular screw, implants. Such a device type may also comprise other components, such as transversal connection bars, not described here but which may be included in the device according to the invention. Due to its advantages in terms of size and easy implantation in reduced spaces, such a device is particularly suitable for entirely internal fitting, i.e. with no part protruding outside the epidermis after the operation. This most frequently consists of a permanent device or one to be kept for a long time.

Figure 1:
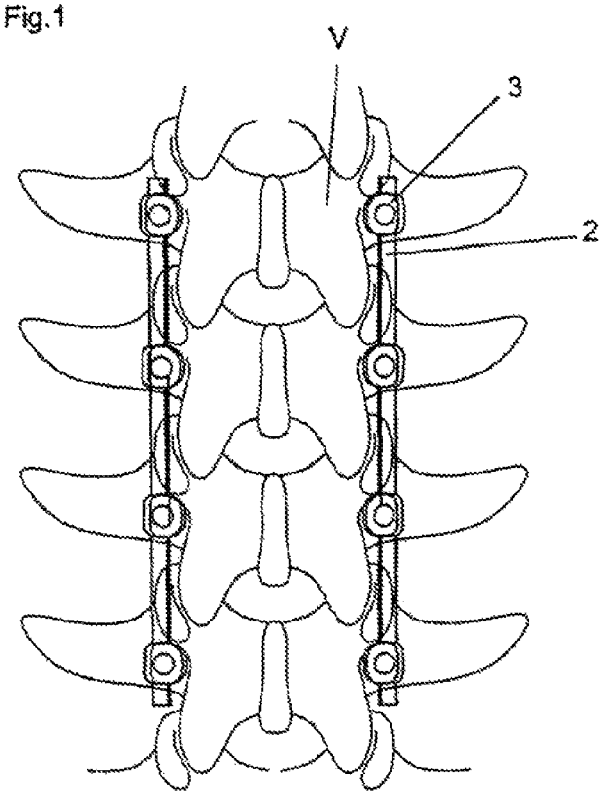
FIG. 1 is a rear view on the spine of an osteosynthesis device according to the invention, in the case of pedicular screw implants.
Figure 2:
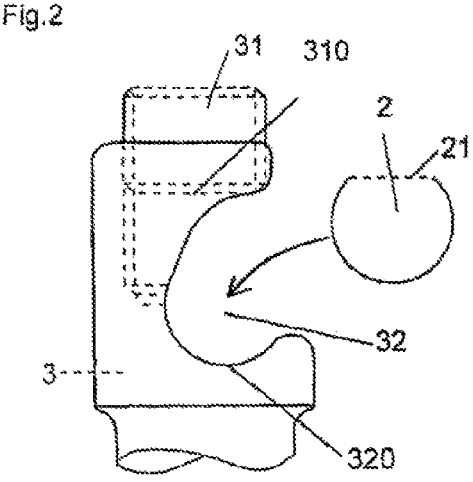
FIG. 2 is a partial side view of the region comprising the fixation of a bar to an implant, at the stage where the bar is presented at the entry of the opening of the implant and where the clamping screw is pre-fitted in the implant.
Figure 3A:
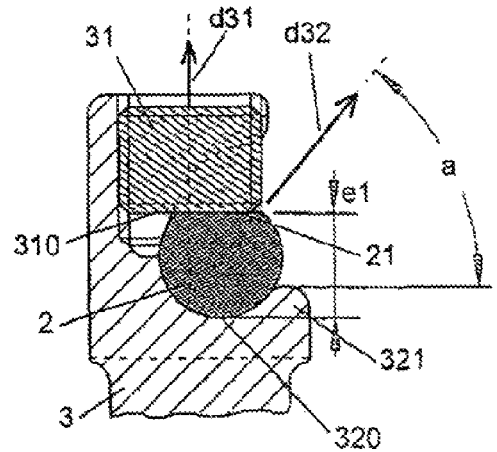
FIGS. 3a and 5 are section side views of a device according to the invention, at the axis of an implant, in an embodiment using a bar comprising a single flat part and for two different bar thicknesses.
Figure 5:
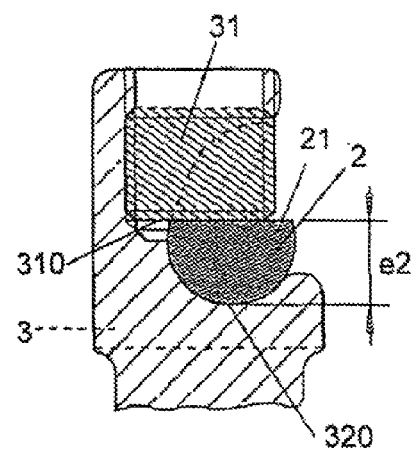

In an embodiment represented in FIGS. 2, 3a and 5, the bar 2 has a rounded cross-section comprising a flat part 21. Said flat part forms a transversal bearing surface, i.e. enabling clamping by supporting the clamping means on said surface, in a direction approximately perpendicular to the longitudinal axis of the bar 2. In its part comprising the fixation means to the bar 2, the implant 3 comprises an opening in the form of a channel 32 passing through the implant along the axis of the bar. Said channel is open on one side of the implant and comprises in one of its edges clamping means moving along an axis perpendicular to the axis of the channel and the bar 2.

Once inserted into the channel 32 of the implant 3, the bar is held by clamping against an internal wall 320 of the channel using clamping means, said means possibly being a clamping screw 31 co-operating with a threaded hole. In the embodiments illustrated in FIGS. 1 to 6, the clamping screw 31 comprises a plane part 310 at its end pressing on the flat part 31 of the bar. As a general rule, said clamping screw may advantageously be of a set screw type so as to minimize its size while retaining the possibility of a long movement along its axis. Said screw comprises gripping means, such as an upper face comprising a recess 312, FIGS. 7 and 8, capable of co-operating with a maneuvering or clamping tool, for example a hexagon socket recess.

In the embodiments described here, the body of the implant is attached to the bone anchorage means, whether they consist of a threaded part (FIG. 6) or one or more hooks (not shown). In this case, the body of the implant itself comprises the clamping means and receives the support bar(s) 2, by direct contact or via intermediate support parts such as rings or distance sleeves.

In the embodiment described here, the clamping screw 31 is screwed into a threaded hole passing through the top edge of the channel 32 and does not overlap onto the opening of said channel and therefore does not obstruct the insertion of the bar 2. Therefore, the clamping screw 31 can be pre-fitted in the implant, thus decreasing the operations during the intervention, the operating time and the risk of the part being lost in the operative field.

Due to the plane contact between the clamping screw 31 and the bar 2, it is possible to use several types of bars, of different thicknesses e1, FIG. 3; e2, FIG. 5, in the same implant model, provided that the cross-section of the bar 2 is of a shape capable of co-operating with the lower wall 320 of the implant channel. Indeed, due to the plane nature of the contact surface 21 of the bar, the clamping screw 31 will clamp the bar 2 in the same way, irrespective of its thickness, provided that its travel is sufficient to come into contact with the flat part 21. Therefore, it is possible to have different bar thicknesses, and therefore different rigidities, for the same implant model, which reduces the stock and type of productions required to cover all requirements. It is also possible to modify rigidity by changing the bar during the operation or during a subsequent operation according to the performances obtained, without having to change the implants, which could represent an injury or additional damage to the vertebrae.

Figure 4A:
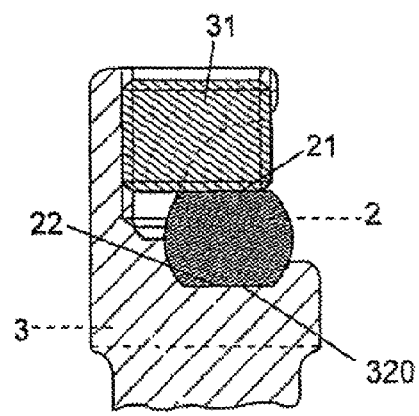
FIG. 4a is a side view of a device according to the invention, at the axis of an implant, in an embodiment using a bar comprising two flat parts.

In another embodiment represented in FIG. 4a, the bar 2 comprises a second flat part 22 opposite the first flat part 21 and approximately parallel to said part, said second flat part 22 forming a bearing surface on the bottom face 320 of the channel 32 of the implant 3. In this arrangement, by means of its co-operation with the wall 320 of the channel, the second flat part 22 of the bar helps ensure the stability and centering of said bar in the channel 32 of the implant during clamping to ensure that the clamping screw 31 is indeed resting perpendicularly on the flat part 21 and therefore provides the best clamping possible. Through this increased stability, this arrangement also ensures improved subsequent reliability of the clamping, by preventing the bar 2 from pivoting around its axis under the effect of forces or vibrations, which would be liable to cause the loosening of the assembly.

In one embodiment, the channel 32 receiving the bar 2 in the implant 3 is of a shape enabling the extension of the bar along an outward direction d32 forming a non-null angle a with a plane perpendicular to the axis of the clamping means 31. To prevent any untimely escape of the bar from the implant, said angle a is oriented in the direction where the outward direction d32 of the bar forms an acute angle with the loosening direction d31 of the clamping means. This means that the clamping means 31 must move in the loosening direction d31 for the bar to be able to move d32 to the channel outlet.

Figure 3B:
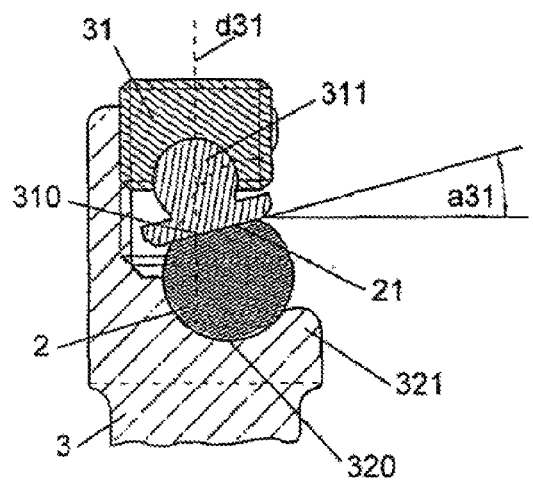
FIG. 3b is a sectional side view of a device according to the invention, at the axis of an implant, in an embodiment comprising a polyaxial clamping screw.

In one embodiment represented in FIG. 3b, the clamping screw 31 comprises a plane bearing surface 310 mounted on a ball joint 311, enabling perfectly flat support on the bar, even if the flat part is not exactly perpendicular to the axis of said clamping screw, in particular when the axes of the different implants are not perfectly parallel. The permissible angle a31 of inclination may for example be of the order of 20 degrees.

The clamping means may be immobilized by any known means, such as glue, the plastic deformation at one or more points of the surfaces co-operating for their movement, or the presence of elastically deformable substances in the threading such as a "Nyl'stop" type locking ring. The only micro-movements remaining possible for the bar are then, at the most, limited to the plane perpendicular to the axis d31 of the clamping means. The movements in this plane, particularly when moving from the base of the channel, are themselves restricted by a part of the bottom edge of the channel, forming an upward nose 321 opposing these movements.

Figure 4B:
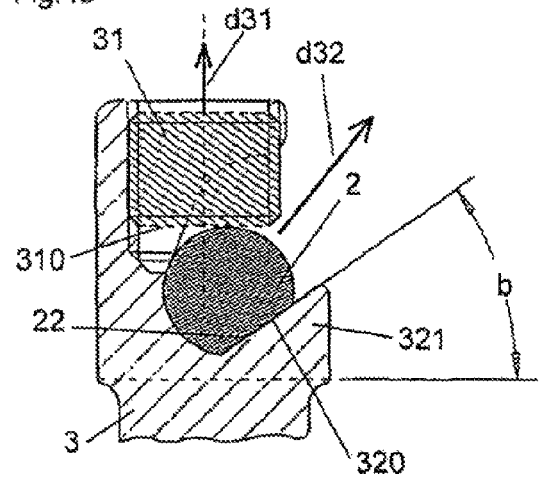
FIG. 4b is a side view of a device according to the invention, at the axis of an implant, in an embodiment using a bar comprising one flat part and an implant comprising an inclined plane surface.

In one embodiment represented in FIG. 4b, the bar 2 comprises a flat part 22 which co-operates with the inner wall 320 of the channel 32 of the implant forming a plane surface, thus ensuring the stability and centering of said bar in the channel 32 of the implant during the clamping of the clamping screw 31. Said plane surface 320 of the implant forms a non-null angle b with a plane perpendicular to the axis d31 of the clamping means. So as to prevent any untimely escape of the bar from the implant, said angle b is oriented in the direction where the outward direction d32 of the bar forms an acute angle with the loosening direction d31 of the clamping means. This means that the clamping means 31 must move in the loosening direction d31 for the bar to be able to move d32 to the channel outlet.

Figure 6:
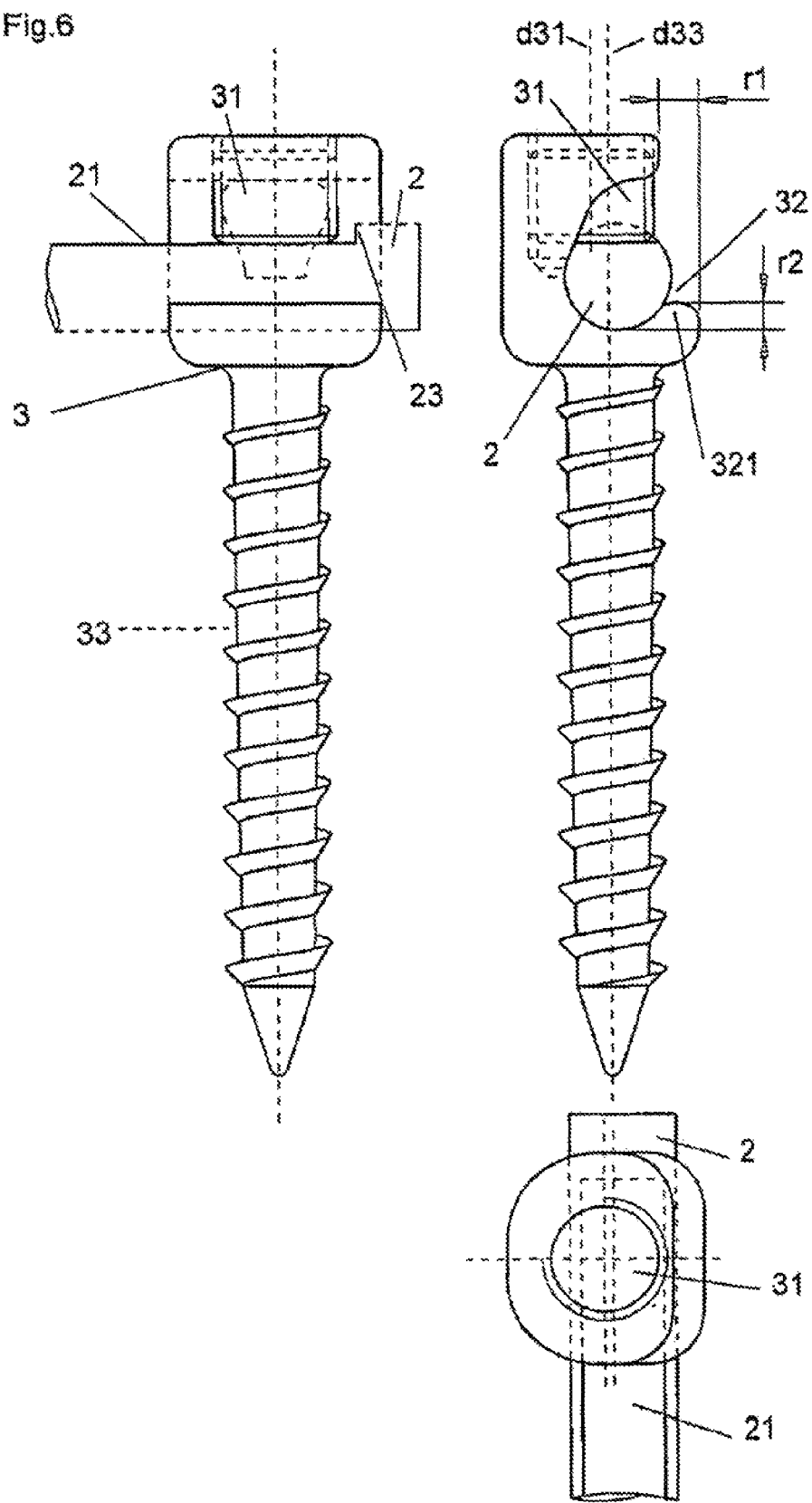
FIG. 6 is a side and top view of an implant according to the invention, in an embodiment using a bar comprising an end with no flat part, in the case of a screw implant.

In one embodiment illustrated in FIG. 6, the support bar 2 comprises one end, or two, comprising no flat part 21. The end of the flat part in this case forms a shoulder 23 which ensures that the bar 2 does not escape from the implant in a direction longitudinal to said bar. Due to this safety device, it is possible only to allow a very short length of bar 2 to protrude from the implant, which reduces the size of the overall device and improves its implantation possibilities at points where anatomical conditions allow little space.

In one embodiment represented in FIG. 6, the implant 3 comprises bone anchorage means composed of one part 33 tapered and threaded in a known way, the bar fixation means and clamping means 31 are in this case located in the end opposite the bone anchorage means. In this embodiment, the axis d31 of the clamping means is parallel to the axis d33 of the bone anchorage means, the clamping being carried out by moving closer to the threaded part, referred to here as the lower part of the implant 3. So as to limit the size of the implant, the axis of the clamping means may be offset by moving away from the inlet of the channel 32 to insert the bar 2 in the implant. In the same way, the top edge of the channel comprises a recess r1 in relation to the bottom edge in its projection along the axis d33 of the implant. Said recess r1 could typically be of the order of 2 mm. So as to provide sufficient clamping, the nose 321 formed by the bottom end of the channel 32 protrudes upwards by a determined height r2 in relation to the plane perpendicular to the axis d31 of the clamping means and via the bottom part of the wall 320 which supports the bar 2 during clamping. Said height r2 could typically be of the order of 2 mm.

For the implantation of an osteosynthesis device according to the method according to the invention, several types of implants, for example screwed or comprising a hook, may be used.

In the case (represented in FIG. 1) of screwed implants, this implantation may be carried out in the part of the vertebra referred to as the pedicle. This type of surgical intervention comprises in this case a step consisting of fixing by screwing the part of the implant 3 provided with a screw pitch 33 on the vertebrae V, for example two implants on each of five vertebrae, by aligning the directions of their respective channels upwards.

During a surgical intervention, if an osteosynthesis device is implanted using the method according to the invention, the use of bars 2 comprising one or more flat parts 21, 22 enables said bars to offer a determined flexibility along a direction perpendicular to said plane faces. Said flexibility is important when bending the bars, necessary to adapt the entire device to the patient's conformation and the modifications that need to be made. The presence of said plane faces also enables the bars to comprise a plane surface on part of their length to comprise accurate implant dimensional references or positioning references.

Due to the fact that implants of the same model can accept several bar thicknesses e1, e2, it will be possible to modify the choice of bar rigidity after fixing the implants, without needing to extract said implants from the vertebrae to insert others, therefore also without damaging the vertebrae further in the case of screwed implants.

In a following step of a method according to the invention (represented in FIG. 2), the arrangement of the opening of the channel 32 of the implant 3 makes it possible to insert the bar 2 in a simple lateral movement, without requiring a longitudinal movement along the axis of the bar as in the case of a clamp.

Since the clamping screw 31 is already in place in the implant 3, the clamping can be carried out without assembling additional parts. Since said clamping screw is supported by a plane part 310 on a plane surface 21 of the bar, the contact surface enabling the clamping will be larger than on a round cross-section bar, directly ensuring high reliability of the connection. Once the clamping screw is in place, the raising of the bottom edge of the channel 32 in the form of a nose 321 prevents any lateral movement of the bar outside the channel.

The clamping may be carried out in several stages, a first progression of the clamping screw making it possible to hold the bar in the implant while allowing freedom of longitudinal movements to adjust the position of the implants on the bar, as required. These adjustments may be composed of a positioning of the implants at different distances from the end of the bar, to adjust the position of the spine in a sagittal plane, i.e. in different positions varying in terms of arching (lordosis) or curvature (cyphosis). Said adjustment may also comprise differences in positioning between the implants of each of two bars arranged at either side of the spine, to adjust the position of the spine in a lateral plane, i.e. in different curvatures inclined to varying degrees on one side of the body or in relation to the pelvis.

Once the desired relative positions of the different components of the devices and the spine have been obtained, the bar will be clamped completely in the implant in another step, as required and according to the progress of the surgical intervention, by completely clamping the clamping screw on the flat part 21 of the bar.

The method according to the invention, by reducing the complexity of the assembly, makes it possible in this way to reduce implantation difficulties, rendering the intervention shorter, less tiring for the operative personnel and less traumatizing for the patient. By reducing the size of the device without affecting the reliability of the assembly, it is also possible to obtain better results and use this technique in a larger number of cases. The possibility to change the bars without removing the implants also makes it possible to envisage a modification of the device more easily in order to adjust the performance according to requirements and the results observed.

In other embodiments, the device according to the invention can use one or more bars 2 comprising in part or all of their length a non-plane transversal bearing surface 21. Said bearing surface is produced by a region where part of the circumference of the bar comprises a convexity lower than the convexity of the rest of the circumference of the bar. A lower convexity in this case refers to a convexity comprising a greater radius of curvature. The contact with a plane surface of the clamping screw 31 or clamping means will then be greater than on a circular circumference and more reliable.

Figure 7:
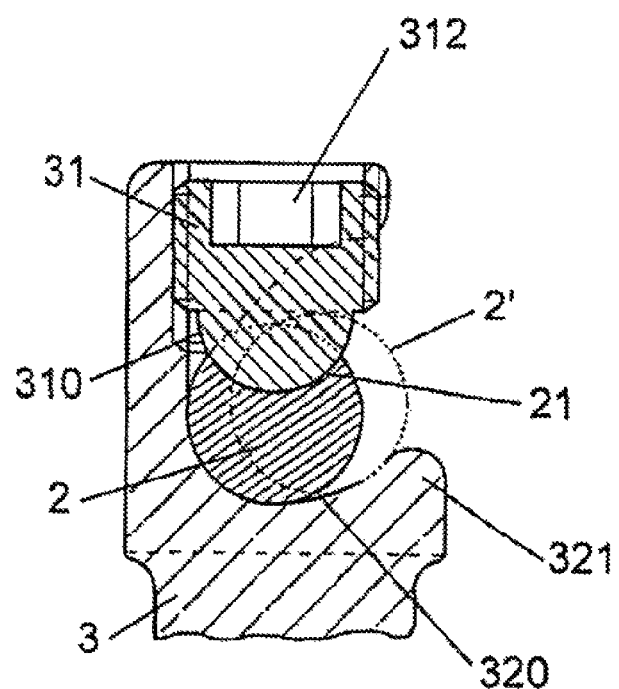
FIG. 7 is a sectional side view of a device according to the invention, at the axis of an implant, in an embodiment using a spherical head clamping screw clamping a bar comprising a recess or a circular cross-section groove complementary to the clamping face.
Figure 8:
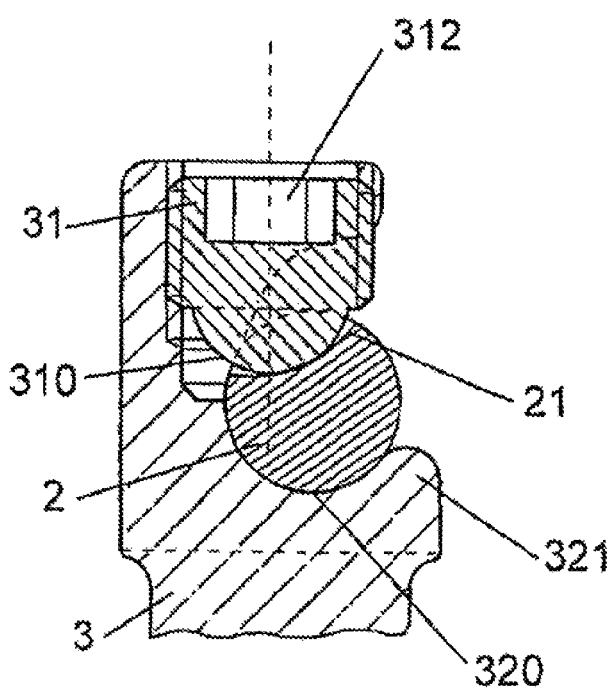
FIG. 8 is a sectional side view of a device according to the invention, at the axis of an implant, in an embodiment using a spherical head clamping screw clamping a bar comprising a recess or a circular cross-section groove of a radius greater than that of the clamping face.

In one embodiment represented in FIGS. 7 and 8, the device according to the invention uses one or more bars 2 comprising a transversal bearing surface 21 showing a face of opposed convexity to the rest of the circumference, i.e. concave. In this embodiment, the clamping means, for example the clamping screw 31, comprise a clamping face 310 showing a convexity in the same direction as the bearing surface 21 of the bar 2. Said clamping surface 310 may in particular show a form of revolution around its screwing axis d31, so that said screwing can be carried out with a progressive approach and a continuous contact on the bar 2.

Depending on the applications, the bar 2 may comprise one or more regions comprising such a transversal bearing surface 21.

Said bearing surfaces may be produced in several regions, contiguous or not, distributed along the bar or on only part of this length. Such a bar may in this way comprise one or more spherical recesses, or oblong recesses with a circular cross-section and spherical ends, or in the form of grooves of circular cross-section transversal to the bar.

Said bearing surfaces may also be produced in several parts of the same section of the bar, i.e. distributed in several different angular positions around the same point located on the axis of the bar. Such a bar may in this way comprise several grooves along its length in different angular positions.

Such position variations thus make it possible to produce a small number of different bar models for numerous anatomical or pathological configurations, by clamping on the most suitable bearing surface. These different clamping point possibilities may also enable easier adjustment of the longitudinal position of the implants in relation to the bar. Indeed, it is possible to insert the bar into the channel of the implant and hold it there by screwing the clamping screw sufficiently, without locking it. The presence of a tapered recess or a plane, convex or concave groove makes it possible to move the implant on the bar before locking.

In the embodiment illustrated in FIG. 7, the clamping surface 310 and the bearing surface 21 comprise approximately complementary cross-sections, transversal to the bar 2. Therefore, clamping is carried out on large contact surface and ensures a good reliability in itself. In this embodiment, the clamping surface 310 may show for example a spherical portion shape. The channel 32 receiving the bar 2 in the body of the implant 3 may then comprise an arc-shaped internal wall 320 wherein the centre coincides with the centre of the clamping 310 and bearing surfaces 21. In this way, it is possible to modify, around said centre, the angular position of the bar in the channel, for example in a slightly offset position 2', to carry out a rotation or de-rotation to adjust the relative angular position of several implants fixed onto the same bar. Due to the arc shape of the internal wall 320 of the base of the channel 32, said adjustment may be carried out without modifying the distance of the bar to the clamping screw and therefore there is no risk of untimely locking or unlocking.

In the embodiment illustrated in FIG. 8, the clamping surface 310 of the clamping screw 31 shows a lower convexity than that of the transversal bearing surface 21 of the bar 2. In this embodiment, the clamping surface 310 may for example show a spherical portion shape. The bearing surface 21 of the bar will show in this case an arc-shaped cross-section, transversal to the bar, of a radius greater than that of the clamping surface 310.

While obtaining a large contact surface between the clamping screw and the bearing surface, such a configuration makes it possible carry out a rotation or de-rotation of the bar to adjust the relative angular position of several implants fixed onto the same bar. It is possible in this case to use a channel 32 wherein the internal wall 320 is complementary to the bar, the angular adjustment of the bar then being possible around the axis of the channel or bar.

In this way, the invention relates to an osteosynthesis device, particularly for the spine by means of internal implantation, comprising firstly one or more bars 2 used to support or move the spine, and secondly at least one implant 3 connecting the bars and the vertebrae V, said implant comprising firstly bone anchorage means attached to the body of said implant and secondly fixation means for said bars, said fixation being carried out by clamping means 31 clamping said bar against the internal walls 320 of a channel 32 formed in said body of the implant 3, characterized in that said bars comprise a transversal bearing surface 21 on at least part of their length, said transversal bearing surface being produced by a section of said bars comprising at least one flat part or part of lower or opposed convexity in relation to the rest of said section.

According to one embodiment, the transversal bearing surface 21 of the bar is composed of at least one concave shaped face, showing the shape of a concave recess or a groove.

According to one embodiment, the clamping means comprise a convex surface which is supported on the recess or groove of the bar 2, thus ensuring good clamping reliability.

According to one embodiment, the transversal bearing surface of the bar is composed of at least one face in the form of a flat part 21.

According to one embodiment, the clamping means comprise a plane surface 310 which is supported on the flat part 21 of the bar 2, thus ensuring good clamping reliability.

According to one embodiment, the clamping means 31 comprise a joint 311, for example a ball joint, between their main body and the plane surface 310 supported on the flat surface 21 of the bar 2, enabling a plane support even if the flat part of the bar forms a non-null angle a31 with a plane perpendicular to the axis d31 of the clamping means.

According to one embodiment, the bars 2 comprise at least one of their ends a part with no flat part or transversal bearing surface over a determined length, said part with no flat part forming a shoulder 23 capable of co-operating with the shape of the implant or clamping means to act as a longitudinal stop on the bars, thus making it possible to reduce the length protruding from the implants 3 located at their ends and therefore to reduce the size of the device.

According to one embodiment, the support bars 2 comprise on a part of their length a plane face 22 co-operating with an internal wall 320 of the channel of the implant forming a plane surface to carry out positioning and stable centering of the bar in said opening.

According to one embodiment, the plane surface 320 of the channel 32 of the implant can form a non-null angle b with a plane perpendicular to 30 the axis d31 of the clamping means, said angle b being oriented in the direction where the clamping means are to be loosened d31 to enable the bar to come out d32 of the base of the channel.

According to one embodiment, the approach distance of the clamping means 31 and the dimensions of the channel 32 of the implant are sufficiently large to receive bars of different thicknesses e1, e2 with the same implant model 3, it being possible to compensate for said differences in thickness with a variation in the position of the clamping means in relation to the opposite wall 320 of the channel.

According to one embodiment, the clamping means 31 are located on only one of the two edges of the channel 32 of the implant 3 and can thus be pre-fitted in the implant without obstructing the insertion of the bar 2 during the surgical intervention.

According to one embodiment, the implant 3 receives the bar 2 in a channel 32 wherein the opening comprises an extension direction d32 forming a non-null angle a with a plane perpendicular to the axis d31 of the clamping means, said angle a being oriented in the direction where the clamping means are to be loosened d31 to enable the bar to come out d32 of the base of the channel.

According to one embodiment, the edge of the channel opposite the clamping means forms a nose 321 which prevents the bar 2 from coming out of the channel 32 perpendicular to the axis of the clamping means 31, for example under the effect of vibrations, wear or crushing of the different surfaces in contact.

According to one embodiment, the clamping means 31 are composed of a clamping screw mounted into a threaded hole passing through one of the edges of the channel 32 receiving the bar 2 in the implant 3.

According to one embodiment, the bone anchorage means of the implant are composed of a tapered and threaded part 33 that can be screwed into a vertebra V, for example into a pedicle.

According to one embodiment, the axis d31 of the clamping screw is approximately parallel to the symmetrical axis d33 of the bone anchorage means of the implant.

According to one embodiment, the top edge of the channel 32 comprising the clamping screw 31 is refracted at the symmetrical axis d33 of the implant in relation to the bottom edge of the channel, limiting the size of the implant in the part-opposite the bone anchorage means.

According to one embodiment, the nose 321 formed by the bottom edge of the channel 32 protrudes by a determined distance r1 in relation to the top edge moving from the axis d33 of the implant and protrudes by a determined distance r2 in relation to the base 320 of the channel, along the axis of the clamping screw and in the loosening direction d31.

According to one embodiment, the bone anchorage means of the implant are composed of a curved part that can be attached to a shape disorder present on a spinal component.

According to one embodiment, the device can be used to perform spinal osteosynthesis in exclusively internal implantation.

The invention also relates to a method to prepare such an osteosynthesis device, characterized in that it comprises a step consisting of inserting the clamping means 31 into the implants 3, said step being carried out prior to the surgical intervention.

It should be clear to those skilled in the art that the present invention allows embodiments in numerous other specific forms without leaving the scope of the invention as claimed. As a result, the present embodiments must be considered as illustrations, but may be modified in the field defined by the scope of the claims attached and the invention must not be limited to the details given above.

The invention claimed is:

1. An osteosynthesis system comprising:
   a plurality of elongated support rods each formed in a shape of a rounded bar having a flat surface extending along at least a portion of a side of the support rod in a longitudinal direction between a first end of the support rod and a second end of the support rod, with each support rod having a different thickness in a cross section of the support rod perpendicular to the longitudinal direction, and with the thickness determined by a distance between the flat surface and a side of the support rod opposite the flat surface, and with each support rod having a different bending rigidity determined by the thickness of the support rod;
   an elongated vertebral implant having a longitudinal axis, the implant comprising
      a first end of the implant, a second end of the implant, and a side disposed between the first end and the second end and extending in a direction of the longitudinal axis,
      a bone screw having threading extending from the first end of the implant in the direction of the longitudinal axis,
      a head disposed at the second end of the implant opposite the first end of the implant, the head comprising
         a channel extending through the head in a direction angular to the longitudinal axis, and
         an opening into the channel disposed on the side of the implant, the opening being sized to admit one of the support rods into the channel from the side of the implant without the first end of the support rod or the second end of the support rod passing through the opening and being oriented to admit one of the support rods into the channel at an angle to the longitudinal axis and at a point between the first end and the second end of the implant, and
      a clamp disposed in the head, the clamp having
         a flat tip disposed at a first end of the clamp and a tool coupler accessible from the second end of the implant,
         an open position in which one of the support rods may pass into the channel from the side of the implant through the opening without the first end of the support rod or the second end of the support rod passing through the opening,
         a semi-closed position in which the clamp is moved toward the first end of the implant sufficiently to block passage of a support rod disposed in the channel out through the opening, and
         a locked position in which the clamp is tightened against a support rod disposed in the channel with the flat tip of the clamp abutting and parallel to the flat surface of the support rod.

2. The osteosynthesis system of claim 1 in which each of the support rods comprises a first shoulder at the first end of the support rod and a second shoulder at the second end of the support rod, with each of the first and second shoulders terminating the flat surface and increasing the thickness at the first end of the support rod and the second end of the support rod.

3. The osteosynthesis system of claim 1 in which each of support rods comprises a first shoulder at the first end of the support rod terminating the flat surface and increasing the thickness at the first end of the support rod.

4. The osteosynthesis system of claim 1 in which movement of the clamp comprises rotation of external threads around the clamp within internal threads of a bore in the head.

5. The system of claim 1 in which the flat tip of the clamp is articulable by a joint.

6. The system of claim 1 in which at least one of the support rods comprises plural flat surfaces extending along at least a portion of the support rod.

7. An osteosynthesis device comprising:
   a rounded rod having a first flat surface extending along a side of the rod;
   an implant comprising a vertebral anchor disposed at a first end of the implant and a head disposed at a second end of the implant;
   a clamp disposed in the head, the clamp comprising a threaded end and a ball joint articulating a flat end with respect to the threaded end, with the clamp having fixation position in which the rod is secured in the head with the flat end of the clamp disposed parallel to the first flat surface of the rod and against the first flat surface of the rod.

8. The device of claim 7 in which the first flat surface is terminated by a portion of the rod having a circular cross section disposed at an end of the rod.

9. The device of claim 7 in which the first flat surface is terminated at each end of the rod by a portion of the rod having a circular cross section.

10. The device of claim 7 in which the clamp is movable by rotation of the threaded end in a threaded bore in the head.

11. The system of claim 7 in which the rounded rod comprises a second flat surfaces extending generally parallel to the first flat surface.

12. An osteosynthesis device comprising:
   a bar having a generally cylindrical shape except for a substantially planar bearing surface extending at least partially along a side of the bar parallel to a longitudinal axis of the cylindrical shape;

an implant having an elongated shape extending along a central axis, the implant comprising
- a threaded end located at a first end of the central axis and a head located at a second end of the central axis opposite the first end,
- a channel extending through the head, the channel having an opening located on a side of the head between the first end and the second end and oriented at an angle to the central axis, and
- a threaded clamp disposed at the second end, the clamp comprising a substantially planar clamping surface, the clamp having a fully open position providing sufficient clearance in the opening of the channel to admit the bar in the channel without either end of the bar passing through the opening, a partially open position in which the bar is loosely retained in the channel, and a clamping position in which the bar is fixed in the channel with the clamping surface flat against the bearing surface.

13. The osteosynthesis device of claim 12 in which an end of the bar has a circular cross section perpendicular to the longitudinal axis of the cylindrical shape.

14. The osteosynthesis device of claim 12 in which each end of the bar has a circular cross section perpendicular to the longitudinal axis of the cylindrical shape.

15. The osteosynthesis device of claim 12 in which the bar comprises plural substantially planar bearing surfaces extending at least partially along a side of the bar parallel to a longitudinal axis of the cylindrical shape.

16. The osteosynthesis device of claim 12 in which the planar clamping surface is articulated by a joint.

* * * * *